United States Patent [19]

Ounanian et al.

[11] Patent Number: 5,290,543
[45] Date of Patent: Mar. 1, 1994

[54] LONG WEARING NAIL ENAMEL TOPCOAT AND RELATED METHODS

[75] Inventors: Hovig Ounanian, Princeton Junction; Joseph DiSomma, Ramsey; Debra Coleman, Piscataway; Robert W. Sandewicz, Spotswood; Anthony Castrogiovanni, Belford, all of N.J.

[73] Assignee: Revlon Consumer Products Corporation, New York, N.Y.

[21] Appl. No.: 946,130

[22] Filed: Sep. 17, 1992

Related U.S. Application Data

[63] Continuation of Ser. No. 690,472, Apr. 24, 1991, abandoned.

[51] Int. Cl.$^5$ ............................................. A61K 7/043
[52] U.S. Cl. .................................. 424/61; 424/78.37; 424/401
[58] Field of Search ...................... 424/61, 401, 78.37; 524/512

[56] References Cited

U.S. PATENT DOCUMENTS

| | | | |
|---|---|---|---|
| 4,179,304 | 12/1979 | Rossomando | 424/61 |
| 4,283,324 | 8/1981 | Duffy | 524/512 |
| 4,798,720 | 1/1989 | Holder | 424/61 |
| 4,919,934 | 4/1990 | Deckner et al. | 424/401 |
| 5,066,484 | 11/1992 | Castrogiovanni | 424/61 |
| 5,093,108 | 3/1992 | Pappas et al. | 424/61 |
| 5,145,670 | 9/1992 | Castrogiovanni | 424/61 |
| 5,145,671 | 9/1992 | Castrogiovanni | 424/61 |

OTHER PUBLICATIONS

Remz, Cosmetics and Toiletries, vol. 103, 70 Dec. (1988). Polymers and Thickness in nail-care products.

*Primary Examiner*—Thurman K. Page
*Assistant Examiner*—Jyothsna Venkat
*Attorney, Agent, or Firm*—Julie Backburn

[57] ABSTRACT

A long wearing nail enamel topcoat and a method for doubling the wear of nail enamel using the topcoat of the invention.

7 Claims, No Drawings

LONG WEARING NAIL ENAMEL TOPCOAT AND RELATED METHODS

This is a continuation of copending application Ser. No. 07/690,472 filed on Apr. 24, 1991, abandoned.

TECHNICAL FIELD

The invention is in the field of nail enamels and nail enamel topcoats.

BACKGROUND OF THE INVENTION

Nail lacquers represent a major portion of the cosmetic market. These products are used to protect and embellish the nails. Many performance expectations are required from nail lacquers, including smooth application, rapid dry time, and a lustrous appearance. Prehaps the most important parameter is wear. The significance and desirability of achieving maximum wear is apparent when the typical manicure regimen is examined. Ideally, a complete manicure consists of one coat of basecoat applied to all bare nailsites, followed by two coats of shaded lacquer, plus at least one coat of a clear topcoat. Obviously, considerable time and effort are required to complete such a treatment. In light of this rather involved procedure, it is reasonable to conclude that it is desirable to prolong the lift of the manicure as much as possible.

Many efforts have been conducted in order to maximize wear of nail lacquers. Much of this effort has been concentrated on the development of longer wearing shaded nail lacquers. Unfortunately, this is a very difficult task to accomplish. Similarly much experimentation has been performed on basecoats in order to extend wear, but this has proben very difficult.

SUMMARY OF THE INVENTION

The invention is directed to a nail enamel topcoat composition comprising:
a) about 0.5–5% ¼ sec. nitrocellulose,
b) about 3–10% ½ sec. nitrocellulose,
c) about 0.5–5% 30–40 sec. nitrocellulose,
d) about 3–10% toluenesulfonamide formaldehyde resin,
e) about 3–8% plasticizer, and
f) about 10–35% solvents and diluents.

The invention is also directed to a method for doubling the length of wear of traditional nail enamels comprising applying the composition of the invention to nails immediately after a manicure and thereafter every other day for the desired life of the manicure.

DETAILED DESCRIPTION

The topcoat composition of the invention, when used according to the procedure designated herein will double the wear of traditional nail enamels. The net result is a manicure free from chips, peels, scratches, and other surface defects. Additionally, observed luster is maintained at a very high level.

The various grades of nitrocellulose are well known in the art and available from a a variety of commercial sources.

The plasticizers suitable for use with the invention include dibutyl phthalate, camphor, dioctyl phthalate, diethyl phthalate, castor oil, acetyl tributyl citrate, glyceryl triacetate, camphor, tricresyl phosphate, butyl phthalate, butyl glycolate, triphenyl phosphate, glyceryl tribenzoate benzyl benzoate, butyl stearate, triethyl citrate, propylene glycol adipate, and so on. The preferred plasticizer is dibutyl phthalate/camphor.

A wide variety of solvents and diluents are suitable including toluene, xylene, heptane, N-butyl acetate, N-butyl alcohol, isopropyl alcohol, etocrylene, dipropylene glycol mono-N-butyl ether, butyl cellosolve, ethyl lactate, amyl acetate, methoxypropanol, acetone, methylisobutyl ketone, ethyl acetate, butyl acetate, butyl cellosolve acetate, light petroleum napthas, PPG-2 butyl ether, and so on.

The topcoat of the invention may also contain a variety of nonessential constituents such as preservatives, humectants, vitamins, herbal extracts, protein hydralyzates, cosmetically-acceptable dyes, UV light absorbers, and so on.

A nail enamel topcoat of the following formula is preferred:

|  | weight % |
| --- | --- |
| Toluene | 30–40 |
| Ethyl acetate | 10–20 |
| N-butyl acetate | 10–20 |
| ¼ sec. nitrocellulose | 5–15 |
| Santolite MHP (toluenesulfonamide/ formaldehyde resin) | 5–15 |
| Isopropyl alcohol | 5–15 |
| Dibutyl phthalate | 1–10 |
| N-butyl alcohol | 1–5 |
| Camphor | 0.5–5 |
| Polyvinyl butyral resin | 0.5–5 |
| ¼ sec. nitrocellulose | 0.5–5 |
| 30–40 sec. nitrocellulose | 0.1–1.5 |
| Etocrylene | 0.1–1.0 |

The invention is also directed to a method for doubling the length of wear of traditional nail enamels comprising applying the composition of the invention to lacquer treated nails immediately after a manicure and thereafter every other day for the desired life of the manicure.

After nail color has been applied, either with out without the use of a basecoat, the one coat of the invention is applied to each nailsite and subsequently on days 2,4,6, etc. for the desired life of the manicure. The net result is a manicure which appears free from chips, peels, scratches, and other surface defects. The topcoat composition of the invention, in addition, provides a very high level of luster.

The invention will be described in connection with the following examples which are set forth for the purposes of illustration only.

EXAMPLE 1

A nail top coat composition was made as follows:

|  | wt % |
| --- | --- |
| Toluene | 33.98 |
| Ethyl acetate | 14.04 |
| N-butyl acetate | 13.58 |
| ¼ sec. RS nitrocellulose | 8.82 |
| Santolite MHP toluenesulfonamide/ formaldehyde resin) | 7.60 |
| Isopropyl alcohol | 7.41 |
| Dibutyl phthalate | 5.00 |
| N-butyl alcohol | 3.00 |
| Camphor | 2.00 |
| Polyvinyl butyral resin | 2.00 |
| ¼ sec. RS nitrocellulose | 1.30 |
| 30–40 sec. RS nitrocellulose | 0.77 |

| | wt % |
|---|---|
| Etocrylene | 0.50 |

*Monsanto

All ingredients were combined by means of a simple mixing procedure. Normal safety procedures were employed because of the presence of volatile solvents. The resulting procedure was a transparent, straw colored liquid of medium viscosity at room temperature.

EXAMPLE 2

A nail enamel top coat was made as follows:

| | w/w % |
|---|---|
| ½ sec. RS nitrocellulose | 9.00 |
| ¼ sec. RS nitrocellulose | 1.50 |
| 30–40 sec. RS nitrocellulose | 0.75 |
| Acetyl tributyl citrate | 7.00 |
| Etocrylene | .025 |
| N-butyl acetate | 36.50 |
| Ethyl acetate | 18.00 |
| Isopropyl alcohol | 5.00 |
| Toluene | 5.00 |
| Sucrose benzoate | 14.50 |
| Sucrose acetate isobutyrate | 2.50 |

EXAMPLE 3

A nail topcoat composition was made as follows:

| | w/w % |
|---|---|
| ½ sec. RS nitrocellulose | 7.00 |
| ¼ sec. RS nitrocellulose | 1.20 |
| 30–40 sec. nitrocellulose | 0.60 |
| Glyceryl triacetate | 5.00 |
| Epoxy resin | 4.00 |
| Polyurethane | 1.00 |
| Toluene | 5.00 |
| Isopropyl alcohol | 3.75 |
| N-butyl acetate | 43.50 |
| Ethyl acetate | 28.95 |

EXAMPLE 4

A nail enamel topcoat composition was made as follows:

| | w/w % |
|---|---|
| ½ sec. RS nitrocellulose | 5.00 |
| ¼ sec. RS nitrocellulose | 10.00 |
| 30–40 sec. RS nitrocellulose | 2.00 |
| Dibutyl phthalate | 6.00 |
| Acrylates copolymer | 10.00 |
| Butadiene/acrylonitrile copolymer | 0.50 |
| Toluene | 10.00 |
| N-butyl acetate | 22.50 |
| Ethyl acetate | 24.00 |
| Ethyl lactate | 2.00 |
| Benzophenone 1 | 0.50 |
| Isopropyl alcohol | 7.50 |

EXAMPLE 5

The nail enamel topcoat of the invention was tested for effectiveness on a number of panelists. Panelists initially applied two coats of nail enamel and one coat of the topcoat composition of the invention. The top coat composition of the invention was sent home with the panelists for application over the weekend. Max Factor Lavender Blues Nail Enamel was used in all studies.

In Test 1 eleven panelists reapplied the topcoat whenever they felt it was necessary. Five of the eleven felt the topcoat achieved twice the wear. Four of the eleven felt the topcoat increased nail enamel wear. Two of the eleven felt the top coat provided nail enamel of equal or less wear.

In Test 2 twelve panelists applied the topcoat every other day. All twelve panelists achieved twice the wear or more of their nail enamel.

In test 3, separately conducted, eleven panelists applied the topcoat every other day. Nine of the eleven achieved twice the wear. One of eleven achieved increased wear. One of eleven achieved equal wear.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the appended claims.

We claim:

1. A nail enamel topcoat composition consisting of:

| | w/w % |
|---|---|
| Toluene | 30–40 |
| Ethyl acetate | 10–20 |
| N-butyl acetate | 10–20 |
| ½ sec. nitrocellulose | 5–15 |
| Santolite MHP | 5–15 |
| (toluene sulfonamide formaldehyde resin) | |
| Isopropyl alcohol | 5–15 |
| Dibutyl phthalate | 1–10 |
| N-butyl alcohol | 1–5 |
| Camphor | 0.5–5 |
| Polyvinyl butyral resin | 0.5–5 |
| ¼ sec. nitrocellulose | 0.5–5 |
| 30–40 sec. nitrocellulose | 0.5–1.5 |

2. A nail enamel topcoat composition consisting of:

| | w/w % |
|---|---|
| ½ sec. RS nitrocellulose | 9.00 |
| ¼ sec. nitrocellulose | 1.50 |
| 30–40 sec. nitrocellulose | 0.75 |
| Acetyl tributyl citrate | 7.00 |
| Etocrylene | .025 |
| N-butyl acetate | 36.50 |
| Ethyl acetate | 18.00 |
| Isopropyl alcohol | 5.00 |
| Toluene | 5.00 |
| Sucrose benzoate | 14.50 |
| Sucrose acetate isobutyrate | 2.50 |

3. A nail enamel topcoat composition consisting of:

| | w/w % |
|---|---|
| ½ sec. RS nitrocellulose | 7.00 |
| ¼ sec. RS nitrocellulose | 1.20 |
| 30–40 sec. RS nitrocellulose | 0.60 |
| Glyceryl triacetate | 5.00 |
| Epoxy resin | 4.00 |
| Polyurethane | 1.00 |
| Toluene | 5.00 |
| Isopropyl alcohol | 3.75 |
| N-butyl acetate | 43.50 |
| Ethyl acetate | 28.95 |

4. A nail enamel topcoat composition consisting of:

|  | w/w % |
| --- | --- |
| ½ sec. RS nitrocellulose | 5.00 |
| ¼ sec. RS nitrocellulose | 10.00 |
| 30–40 sec. RS nitrocellulose | 2.00 |
| Dibutyl phthalate | 6.00 |
| Acrylates polymer | 10.00 |
| Butadiene/acrylate copolymer | 0.50 |
| Toluene | 10.00 |
| N-butyl acetate | 22.50 |
| Ethyl acetate | 24.00 |
| Ethyl lactate | 2.00 |
| Benzophenone-1 | 0.50 |

-continued

|  | w/w % |
| --- | --- |
| Isopropyl alcohol | 7.50 |

5. A method for doubling the length of wear of traditional nail enamels applying the composition of claim 1 to lacquer treated nails immediately after a manicure and thereafter every other day for the desired life of the manicure.

6. The method of claim 5 wherein the nail lacquer is applied using a basecoat.

7. The method of claim 5 wherein the nail lacquer is applied without a basecoat.